US012728228B2

(12) United States Patent
Rottenberg et al.

(10) Patent No.: US 12,728,228 B2
(45) Date of Patent: Sep. 8, 2026

(54) AXIAL SHARP NEEDLE REENTRY DEVICE

(71) Applicant: Bentley Innomed GmbH, Hechingen (DE)

(72) Inventors: Dan Rottenberg, Haifa (IL); Yossi Pesis, Pardes Hana (IL); Avraham Matzkin, Kochav Yair (IL)

(73) Assignee: Bentley InnoMed GmbH, Hechingen (DE)

( * ) Notice: Subject to any disclaimer, the term of this patent is extended or adjusted under 35 U.S.C. 154(b) by 947 days.

(21) Appl. No.: 16/464,270

(22) PCT Filed: Jul. 23, 2018

(86) PCT No.: PCT/IB2018/055460
§ 371 (c)(1),
(2) Date: May 26, 2019

(87) PCT Pub. No.: WO2019/234482
PCT Pub. Date: Dec. 12, 2019

(65) Prior Publication Data

US 2020/0269014 A1 Aug. 27, 2020

Related U.S. Application Data

(60) Provisional application No. 62/680,022, filed on Jun. 4, 2018.

(51) Int. Cl.

| | |
|---|---|
| ***A61M 25/00*** | (2006.01) |
| ***A61M 25/01*** | (2006.01) |
| ***A61M 25/06*** | (2006.01) |

(52) U.S. Cl.
CPC .... *A61M 25/0082* (2013.01); *A61M 25/0069* (2013.01); *A61M 25/0074* (2013.01);
(Continued)

(58) Field of Classification Search
CPC .......... A61M 25/0069; A61M 25/0082; A61M 2025/009; A61M 25/0074;
(Continued)

(56) References Cited

U.S. PATENT DOCUMENTS 6,221,049 B1 4/2001 Selmon et al.
6,514,217 B1 * 2/2003 Selmon .............. A61B 17/3207 600/585
(Continued)

FOREIGN PATENT DOCUMENTS

CN 104010689 8/2014
EP 0829269 3/1998
(Continued)

OTHER PUBLICATIONS

PCT Search Report PCT/IB2018/055460, mailed Apr. 15, 2019.
Japan Notice of Allowance with English translation for Application No. 2020-568280, dated Jan. 31, 2023, 4 pages.

*Primary Examiner* — Chelsea E Stinson
*Assistant Examiner* — Hamza A Darb
(74) *Attorney, Agent, or Firm* — Brooks Kushman P.C.

(57) ABSTRACT

A catheter, such as for use for total occlusion crossing and lumen reentry, incorporate a retractable long flexible nitinol curved needle at the catheter distal end. The needle is straight when withdrawn inside the catheter. When pushed forward, the needle is deployed by protruding axially out, directly from the distal tip, through a mechanism used to direct the curved needle into a specific radial direction. When pushed forward, the needle restores its curved shape and can penetrate the plaque or the media and intimal layers to reenter the true lumen.

8 Claims, 4 Drawing Sheets

(52) U.S. Cl.
CPC ... *A61M 25/0606* (2013.01); *A61M 2025/009* (2013.01); *A61M 2025/0095* (2013.01); *A61M 2025/0197* (2013.01)

(58) Field of Classification Search
CPC ...... A61M 2025/0095; A61M 25/0606; A61M 2025/0197; A61M 5/3291
See application file for complete search history.

(56) References Cited

U.S. PATENT DOCUMENTS

| | | | | |
|---|---|---|---|---|
| 2003/0120195 | A1* | 6/2003 | Milo | A61M 25/01 604/19 |
| 2005/0027263 | A1* | 2/2005 | Woehr | A61M 5/3273 604/263 |
| 2005/0171478 | A1* | 8/2005 | Selmon | A61M 25/01 604/164.01 |
| 2009/0306650 | A1 | 12/2009 | Govari et al. | |
| 2010/0004627 | A1 | 1/2010 | Ludwig | |
| 2012/0265156 | A1* | 10/2012 | Devereux | A61B 17/3478 604/263 |
| 2013/0006282 | A1* | 1/2013 | Wilkinson | A61B 17/22 606/159 |
| 2013/0204226 | A1* | 8/2013 | Keyser | A61M 25/0097 137/511 |
| 2014/0188149 | A1 | 7/2014 | Patel | |
| 2018/0043134 | A1 | 2/2018 | Alvarez et al. | |

FOREIGN PATENT DOCUMENTS

| | | | |
|---|---|---|---|
| JP | 2002507458 | A | 3/2002 |
| JP | 2012525181 | A | 10/2012 |
| JP | 2017523880 | A | 8/2017 |
| WO | 99/49793 | | 10/1999 |
| WO | 2004/093960 | | 11/2004 |
| WO | 2006/105244 | | 10/2006 |
| WO | 2013/003757 | | 1/2013 |
| WO | 2016/154403 | | 9/2016 |
| WO | 2017/053161 | | 3/2017 |

* cited by examiner

AXIAL SHARP NEEDLE REENTRY DEVICE

FIELD OF THE INVENTION

The present invention relates generally to crossing devices and methods for crossing total occlusions in blood vessels, and/or reentry from one lumen into another lumen, such as but not limited to, reentry into a true lumen of a blood vessel from the extraluminal or sub-intimal space of the vessel.

BACKGROUND OF THE INVENTION

Chronic Total Occlusion (CTO) is an arterial vessel blockage (typically of plaque) that obstructs blood flow. CTO can occur both in coronary and peripheral arteries, and generally results from the same underlying cause—atherosclerosis.

One of the main difficulties in crossing a total occlusion is that the clinician does not know exactly how hard the plaque is until steering a guidewire to the occlusion. If the occlusion is relatively new, the plaque is likely to be soft enough and the guidewire may penetrate the plaque. However, after several weeks or months, the occlusion becomes fibrotic and calcified and the plaque becomes much harder, rendering guidewire crossing of the occlusion difficult if not impossible. Failure to cross the obstruction is the primary failure mode for CTO recanalization.

Another problem is that the CTO blocks contrast agents from flowing through the artery past the obstruction, preventing use of fluoroscopy to guide the guidewire. This increases the risk of perforating or dissecting the vessel, and may possibly increase the risk of tamponade—blood leaking out of the artery around the heart or peripheral organ. Even crossing a partially occluded blood vessel, especially long and/or curved occlusions, can be difficult and time consuming.

However, techniques have been developed for crossing hard total occlusions, starting with simple support catheters like SPECTRANETICS QUICK-CROSS catheter, which is a single lumen tube that supports the guidewire inserted through that lumen, and the REALFLOW WINGMAN catheter that includes a straight needle tip that can protrude from the catheter distal tip. Other crossing tools are, for example, catheters based on laser energy like the SPECTRANETICS TURBO-ELITE catheter, or BARD CROSSER catheter that is based on ultrasonic vibration to support the guidewire to pass through the plaque. Other mechanical crossing devices, like the BSC TRUEPASS and MEDTRONIC JETSTREAM are based on mechanical drilling through the plaque.

Most crossing devices advance directly in an axial direction relative to the catheter and do not allow any guidewire change of direction if required.

As is well known in anatomy, arteries generally have three coats or layers: an internal or endothelial coat (tunica intima of Kölliker); a middle or muscular coat (tunica media); and an external or connective-tissue coat (tunica adventitia). The two inner coats together are easily separated from the external adventitial layer, and the two inner coats are sometimes referred together as the intimal layer rather than the medial and intimal layers. It is known in the art that during an attempt to get past an occlusion with a guidewire, the guidewire sometimes inadvertently penetrates into the subintimal space between the intimal layer and the adventitial layer of the blood vessel as it attempts to cross the occlusion. Once in the subintimal space, it is very difficult and, in many cases, impossible to direct the guidewire back into the blood vessel true lumen beyond the occlusion.

However, techniques have been developed for entering the subintimal space on purpose and reentering the true lumen after the occlusion. This so-called subintimal recanalization can be a useful procedure, especially when using drug eluting stents, and is widely used. One of the advantages of subintimal recanalization is that a dissection of the subintimal space is more likely to produce a smooth lumen and improved blood flow than a lumen produced by plowing through calcified plaque. However, technical failure occurs in about 20% of patients undergoing percutaneous intentional extraluminal recanalization, many due to the inability to reenter the distal true lumen.

If during percutaneous extraluminal recanalization, the true lumen cannot be reentered with guidewire manipulation, a true lumen reentry device must be used. Currently there are four specially designed reentry devices in the market.

The PIONEER reentry catheter (from MEDTRONIC, Santa Rosa, CA, US and afterwards owned by VOLCANO) is a 7 Fr. intravascular ultrasound (IVUS) device that is placed in the dissection beyond the occlusion. The IVUS image provides an image of the vessel wall. The catheter is constructed with a monorail lumen for delivery of the device over a 0.014 inch wire, and a second wire lumen through the end of the catheter, which ends in a curved nitinol needle that can retract into the catheter near the distal end. The needle is deployed by sliding it out of a distal side port at the side of the catheter just proximal to the IVUS transducer. The IVUS device is used to ultrasonically guide, turn and manipulate the curved needle to arrive at the correct radial orientation for reentry into the true lumen.

The OUTBACK reentry catheter (CORDIS, Miami Lakes, FL, US) is a 6 Fr. catheter with a retractable nitinol curved needle at the distal end. The needle is straight when withdrawn in the catheter. When pushed forward, the needle is deployed by sliding it out of a side port at the side of the catheter just proximal to the catheter distal tip. When pushed forward, the needle restores its curved shape and can penetrate the medial and intimal layers to reenter the true lumen. The rotational orientation of needle deployment is provided by fluoroscopic L- and T-shaped guiding markers on the catheter.

The OFF-ROAD reentry device (BOSTON SCIENTIFIC, US) is a 6Fr. balloon catheter with inner flexible metal straight needle. The balloon is a conical balloon having its flat base in the distal direction. The balloon tends toward the true lumen when inflated, due to stiffness differences between the intimal layer and adventitia layer. The flexible needle is than pushed forward out from the bent balloon catheter to puncture into the true lumen.

The ENTEER™ Re-entry System (EV3 Inc. US) consists of a catheter and guidewire, enabling the physician to target the true lumen from the subintimal channel. The catheter includes a unique, flat shape, self-oriented balloon inflated in the subintimal space, helping to enable special pre-bent guidewire re-entry into the true lumen. The wire exits a side port on the balloon.

SUMMARY OF THE INVENTION

The present invention seeks to provide a novel device for both total occlusion crossing and lumen reentry, in one device, as is described more in detail hereinbelow.

The crossing catheter of the invention may use a retractable nitinol curved needle at the catheter distal end. The needle is forced to be straight when withdrawn inside the catheter. The needle is deployed by pushing it distally forward from a distal rigid tip (as opposed to the prior art balloon at the distal tip) so that it protrudes axially outwards, directly from the distal tip, as opposed to the prior art in which the needle or wire exits from the side. After protruding only slightly, the needle distal portion is straight or almost straight. However, when further pushed out, the needle starts to get a pre-shaped curve to allow future guidewire steering in the occlusion and/or true-lumen reentry.

The catheter of the invention does not use a side port to define the needle direction. Rather, several other mechanisms may be used, such as: 1) an elliptical shaped distal catheter tip lumen section is used to direct the round curved needle into a specific radial direction; 2) an elliptical curved needle inside an elliptical catheter distal tip; and/or 3) a round curved needle with a bulge or spline inside a round hollow tube with a suitable groove or slit (for keying the needle to be at a specific orientation).

Alternatively, no mechanism is used to force a certain radial direction, and the needle is free to rotate inside the catheter shaft, as explained further below.

When pushed forward, the needle advances a few millimeters axially, and only afterwards the needle starts to restore its curved shape and can penetrate the plaque at an angle, either for crossing the occlusion, or for piercing the media and intimal layers to reenter the true lumen. The rotational orientation of needle deployment may be provided by rotating the whole catheter and/or rotating only the needle, according to fluoroscopic guiding markers on or inside the catheter tip or directly on the needle distal section.

The present invention has many applications, such as but not limited to, hard occlusion crossing, hard curved or twisted occlusion crossing, flush occlusion crossing, in-stent restenosis crossing, puncturing stent grafts to open side vessels blood flow, true lumen reentry in PTA (percutaneous transluminal angioplasty), PTCA (percutaneous transluminal coronary angioplasty), and any other percutaneous or non-percutaneous placement of a catheter between two adjacent layers of vessels, arteries, soft tissue, or any other human tissue.

In one embodiment of the invention, a device is provided for reentry into a true lumen of a blood vessel from the extraluminal or sub-intimal space of the vessel.

The invention assists the clinician (e.g., cardiologist, radiologist, vascular surgeons or any other medical doctor who engages in angioplasty procedures) in treating total occlusions and can be used to cross both new and soft plaque and old and hard plaque.

There is provided in accordance with an embodiment of the invention a crossing and lumen reentry device including a single lumen catheter and long flexible needle inside that single catheter lumen. The catheter distal tip is stiff enough to hold the pre-curved needle straight. Only when pushed forward out of the catheter distal tip, the curved needle can regain its curved shape.

In a non-limiting embodiment of the invention, a nitinol needle is disposed in the catheter lumen and a guidewire passes through an internal cavity of the needle. A distal end of the needle is adapted to pierce through plaque or through at least one of the layers to enter the body lumen, and is shaped as lancet sharp tip or alike.

The needle may enter the rigid catheter distal tip in an eccentric round hole; this hole may expand to a large elliptical hole that forces the pre-curved needle to protrude out the catheter at a certain radial direction. The physician may use radiopaque markers on the catheter tip to rotate the catheter to aim the needle protrusion inside the occlusion or towards the blood vessel true lumen.

Alternatively, the needle may enter the rigid catheter distal tip with a ridge or bulge on the needle sliding inside a slot or groove in the catheter rigid distal tip. In this design, the radiopaque markers can be on the catheter distal section or directly on the needle distal section.

Alternatively, the needle may enter the rigid catheter distal tip with both the needle and the catheter distal tip being elliptical rather than circular. The elliptical matching shapes force the pre-curved needle to protrude out the catheter at a certain radial direction.

Alternatively, the needle and catheter do not have any radial orientation mechanism, and the needle can rotate freely inside the catheter shaft, such as by rotating a knob in the handle. Radiopaque markers on the needle distal section, proximal to the curved needle tip, may be used to indicate the needle curve radial direction. To reduce friction between the catheter distal tip and the curved needle which is forced to be straight inside the distal tip, the distal tip may be able to rotate together with the needle relative to the catheter shaft.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
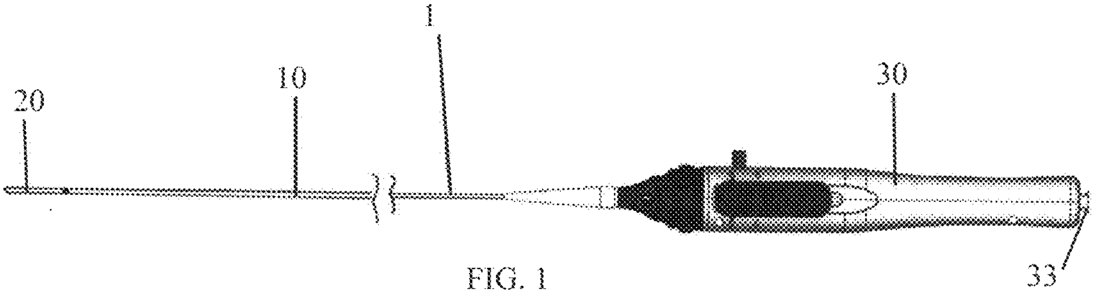
FIG. 1 is a simplified illustration of a crossing catheter device, constructed and operative in accordance with an embodiment of the present invention.

Reference is now made to FIG. 1, which illustrates a crossing catheter and a lumen reentry catheter device 1, constructed and operative in accordance with an embodiment of the present invention. Catheter device 1 includes a catheter shaft 10 which has a rigid distal portion 20 and a handle 30 coupled to the proximal portion of shaft 10. Catheter shaft 10 is formed with a lumen for passing therethrough a long, flexible, pre-shaped needle 40 (not shown in FIG. 1, but seen in FIGS. 2A and 2B and other figures).

Catheter shaft 10 may be fabricated from polyimide, polyurethane, PEBAX (polyether block amide), nylon or other polymers known in the art. Shaft 10 is preferably reinforced with or made from braded metal wires, or polymers reinforced with metal wires braid or springs, as is known in the art, to achieve good torque-ability required for crossing or for reentry catheter radial orientation.

Without limitation, the length of reentry device 1 is 100-180 cm, and its shaft and distal tip diameter is preferably no more than 2.0 mm (6 Fr).

Figure 2A:
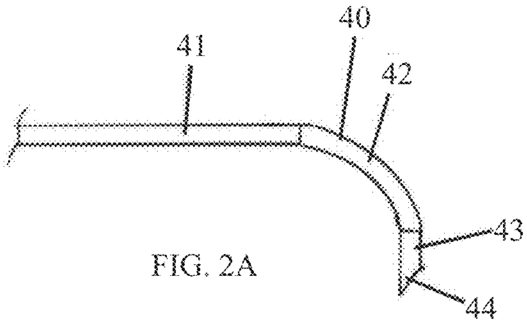
FIGS. 2A and 2B are illustrations of the catheter curved needle.
Figure 2B:
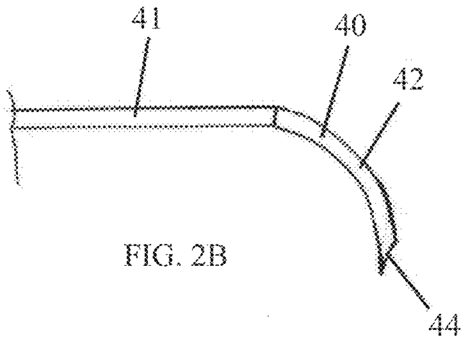

Reference is now made to FIG. 2A, which illustrates the curved, pre-shaped needle 40. Needle 40 may be constructed from a shape memory alloy, such as nitinol, and may or may not be hollow. Needle 40 may include a long straight (preferably, but not necessarily, hollow) section 41, which may be connected to a luer 33, disposed in the handle 30 (not shown here but shown in FIG. 1). A pre-formed, curved section 42 extends distally from straight section 41. The radius of curvature of curved section 42 may be, without limitation, between 5 to 15 mm. curved section 42 may subtend an angle, without limitation, in the range of 30-120°, more preferably in the range of 30-90°, and even more preferably in the range of 60-90°. A short distal straight segment 43 may extend distally from curved section 42; segment 43 may have, without limitation, a length of 2 to 4 mm. The distalmost tip 44 of needle 40 may be a lancet tip 44. Alternatively, as seen in FIG. 2B, needle 40 does not include straight section 43, and curved section 42 ends with the needle lancet tip 44.

Figure 3:
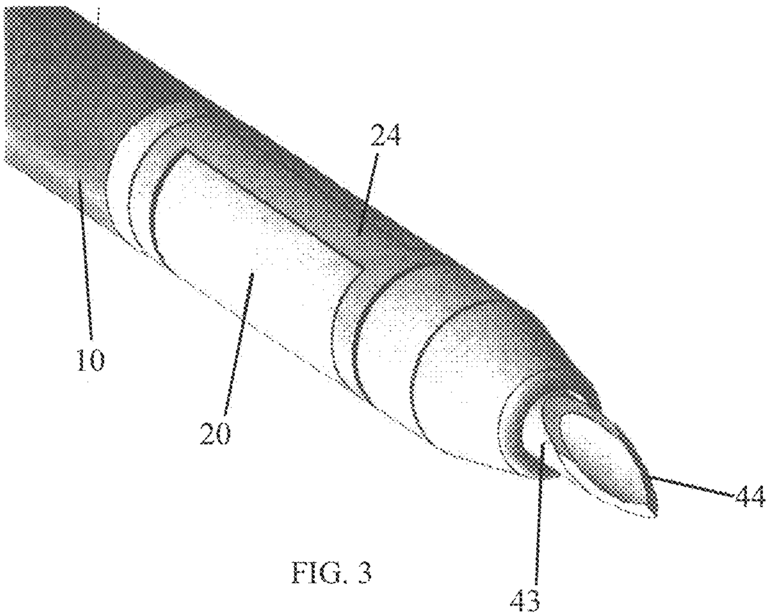
FIG. 3 is an illustration of the crossing catheter device with only the curved needle tip protruding straight from the catheter tip.

Reference is now made to FIG. 3, which illustrates the distal straight section 43 as it just starts to protrude from distal portion 20 of catheter shaft 10. As seen here, when initially advanced distally (pushed forward), such as a few millimeters, the straight section 43 and distal tip 44 protrude straight (axially) out of distal rigid portion 20. In the embodiment of FIG. 2B, which has no straight section 43, the needle 40 starts to regain its curved shape when the distal tip 44 initially starts to protrude from distal rigid tip 20.

As seen in FIG. 3, fluoroscopic or radiopaque guiding markers 24 may be disposed on the distal tip 20 or other portion of catheter shaft 10. For example, markers 24 may be made of platinum, platinum-iridium, tantalum, or tantalum-tungsten or similar alloys that are radiopaque.

Rigid distal tip 20 is preferably made from a rigid biocompatible material, e.g., metal such as stainless steel. The material is sufficiently strong to maintain the distal section 42 of pre-curved flexible needle 40 straight when it does not protrude from tip 20.

Figure 4:
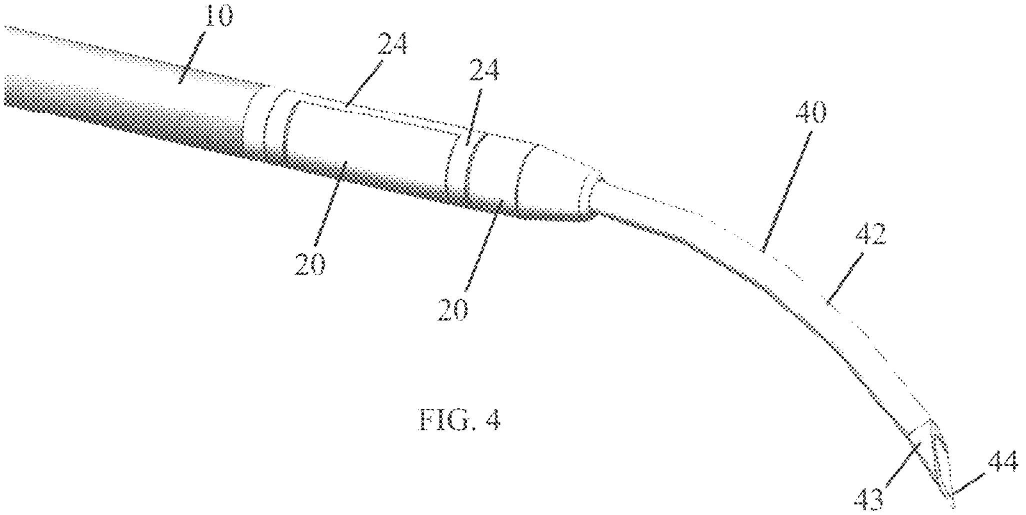
FIG. 4 is an illustration of the crossing catheter device with the curved needle fully protruding out from the catheter distal end.
Figure 5A:
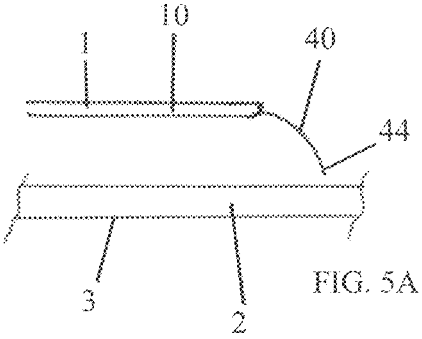
FIG. 5A is an illustration of the fully protruded needle distanced from the true lumen.

Reference is now made to FIGS. 4 and 5A, which illustrates needle 40 at complete or almost complete deployment (protrusion) from distal portion 20 of catheter shaft 10. In this orientation, needle 40 is restored to its curved shape and can penetrate plaque at an angle, for crossing an occlusion, or for piercing and entering the media and intimal layers and afterwards to reenter a true lumen 2 of a blood vessel 3 (FIG. 5A). For crossing, the needle 40 is pushed out the required amount to aim the guidewire to the required direction, which depends on the occlusion curvature and location relative to the rigid tip 20. For reentry into the true lumen, the curved needle 40 may be pushed maximum forward, and can be slowly pulled back proximally if the needle has passed the true lumen, until the distal tip of the needle is positioned in the true lumen.

Figure 5B:
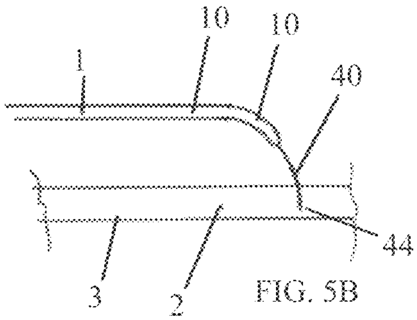
FIG. 5B illustrates the needle tip reaching the true lumen after the entire catheter is pushed forward with needle fully protruded.

Reference is now made to FIG. 5B. If the needle tip 44, even when fully protruded, does not reach the true lumen 2 due to thick vessel walls or a lot of calcific space between the catheter shaft 10 and true lumen 2, the device 1 of the invention, unlike all other reentry devices, allows the user to advance the catheter shaft 10 distally along the needle 40 while fully or partially protruded. The catheter with the protruded needle can then be re-advanced distally and radially, following the direction of the curved needle 42, until it pierces and reenters the true lumen 2.

The rotational orientation of needle deployment is provided by rotating the catheter according to the guiding markers 24 on the catheter tip 20. After final positioning of the needle 40, a guidewire can be pushed forward from the needle tip 44 to continue the procedure.

Figure 6:
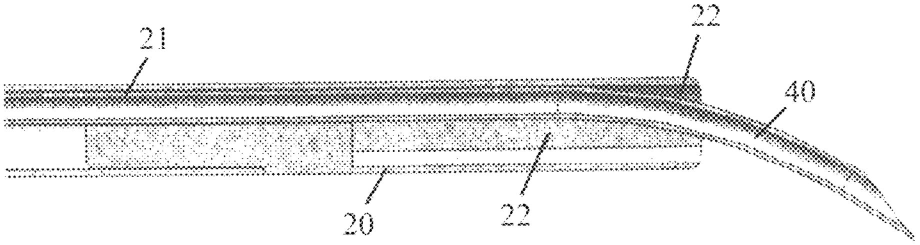
FIG. 6 is a simplified, partially sectional illustration of the flexible needle disposed in the distal rigid tip, in which the needle passes through a lumen, which changes from a circular to elliptical shape.
Figure 7:
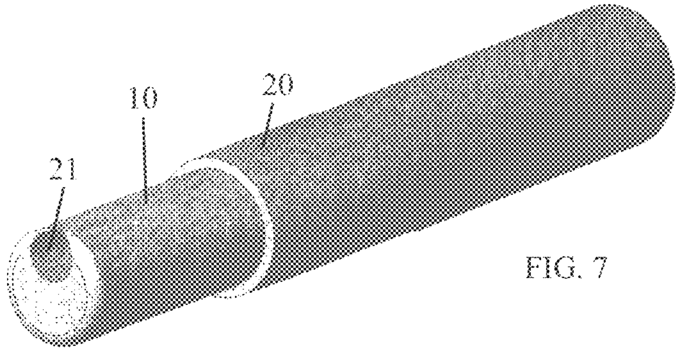
FIG. 7 is a simplified, partially sectional illustration of the lumen reentry catheter distal rigid tip, seen from its proximal side, showing the proximal eccentric needle hole.
Figure 8:
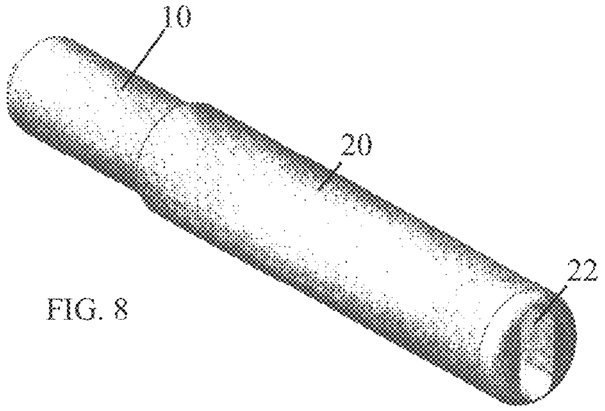
FIG. 8 is a simplified, partially sectional illustration of the lumen reentry catheter distal rigid tip, seen from its distal side, showing the distal elliptical needle exit hole.

Reference is now made to FIGS. 6-8. The distal tip 20 may be formed with an eccentric hole 21 (FIGS. 6 and 7). The eccentric hole 21 may have a constant, uniform size (for example, an elliptical hole or round, circular hole) along its entire axial length up to and including its open end at the distal end of tip 20. Alternatively, eccentric hole 21 may have a relatively smaller size at a proximal end thereof (e.g., circular or elliptical) and a relatively larger size at a distal end thereof. For example, eccentric hole 21 may change its shape to an elliptical larger hole 22 (FIG. 8) at its open end at the distal end of tip 20. The elliptical hole 22 may have a long axis close to the diameter of the catheter shaft 10 and rigid distal tip 20, and a short axis close to the diameter of the round needle 40.

Figure 9:
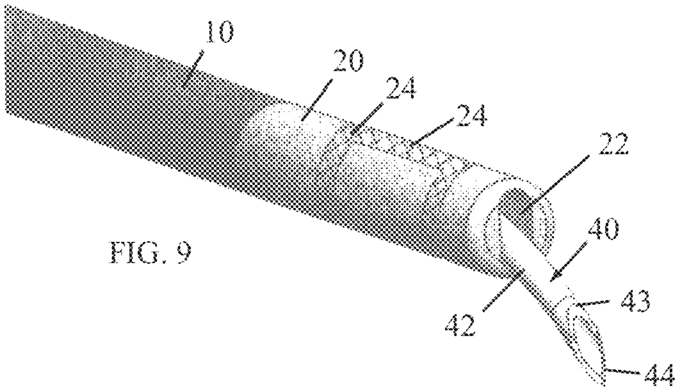
FIG. 9 is a simplified illustration of the lumen reentry catheter distal section, with a radiopaque marker and the pre-curved needle protruding out from the distal tip.

Reference is now made to FIG. 9. When the pre-curved needle 40 is pushed forward from eccentric hole 21 (FIG. 7) into elliptical hole 22, the first straight needle segment 43 protrudes straight forward (distally), and then the curved section 42 starts to curve as much as the elliptical hole 22 allows, and then, when pushed further forward, curved section 42 bends in the direction forced by the elliptical hole 22, which is the opposite direction of the eccentric hole 21 direction (opposite in that it is on the opposite side of the central axis of shaft 10).

As mentioned above, the curved needle 40 needs to be oriented at the desired guidewire crossing direction, or from the sub-intimal space into the blood vessel true lumen. The physician needs to rotate the catheter to aim the needle 40 so that it will point in the required radial direction towards the occlusion, or towards the radial direction of the true lumen, before starting the needle protrusion. The markers 24 on rigid tip 20 or on shaft 10 assist the physician to properly aim the needle. Different markers can be used, as known in the art, for example I, L and/or T shaped markers.

Figure 10A:
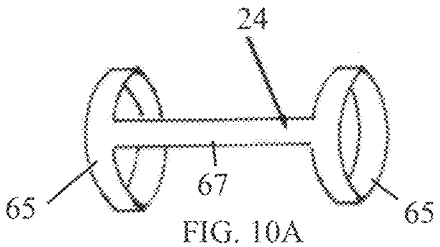
FIG. 10A is an illustration of the radiopaque marker on the catheter distal tip or needle distal section and FIGS. 10B, 10C, and 10D are illustrations of different angiographic views of the markers at different rotation angles.
Figure 10B:
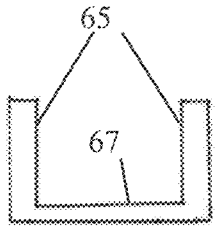
Figure 10C:
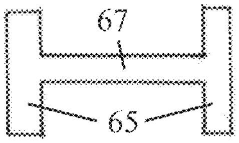
Figure 10D:
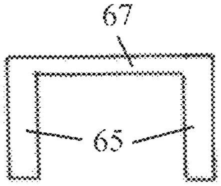

FIGS. 10A-10D illustrate examples of angiography markers 24 that may be used for the needle radial orientation. In FIG. 10A, a marker includes two rings 65 connected by a central beam 67. The marker can be seen angiographically as the letter U (when viewed horizontally) or the letter C (when viewed vertically) [FIG. 10B], letter H (when viewed horizontally) or the letter I (when viewed vertically) [FIG. 10C], or as an inverted letter U (when viewed horizontally) or inverted letter C (when viewed vertically) [FIG. 10D]. The curved needle bending direction can be set, for example, to align with the opening of the letter C.

Figure 11:
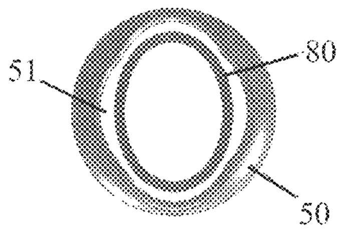
FIG. 11 is a cross-section illustration of the catheter elliptical distal tip with an elliptical needle.

Reference is now made to FIG. 11, which illustrates an alternative rigid tip 50. Rigid tip 50 is formed with an elliptical lumen 51 and the needle has a distal section 80 which has an elliptical shape whose outer contour is similar to the inner contour of elliptical lumen 51. In this manner, the pre-curved needle 40 is forced to protrude out from rigid tip 50 at the orientation of the elliptical shape.

Figure 12:
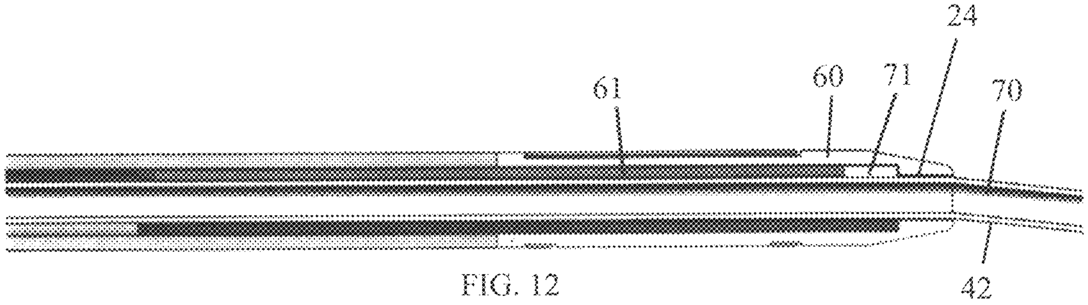
FIG. 12 is an illustration of the crossing catheter distal section with a groove or slot in the rigid distal tip and a bulge or ridge in the needle.

Reference is now made to FIG. 12, which illustrates an alternative rigid tip 60 which together with a needle 70 (which is similar to needle 40) form a keyed configuration for defining the angular orientation of the needle 70. For example, rigid tip 60 or shaft 10 may be formed with a longitudinal slot 61, while needle 70 may include a ridge 71 arranged for sliding in slot 61. Alternatively, slot 61 can be on needle 70 and the ridge 71 can be on tip 60 or shaft 10. Marker 24 can be disposed on catheter tip 60 or needle 70, e.g., proximal to curved needle section 42.

Assembling marker 24 on the needle 40 instead of on the shaft 10 may provide the advantage of reducing the catheter maximal outer diameter. When marker 24 is assembled on reinforced or braided shaft tube, it increases the shaft outer diameter. When assembled on the needle, it will not increase the diameter, as the needle straight section 41 is usually covered by PTFE shrink to reduce friction. It is noted that friction is typically the greatest at the iliac arch area, when using a cross-over approach (getting to the target leg from the other leg, which is the most common technique). Removing a small segment of the PTFE shrink near the straight needle distal end 41 provides enough space for the marker 24, without increasing the total device outer diameter, making it suitable for treating smaller blood vessels.

Assembly of marker 24 directly on the needle distal section, provides also needle axial movement indication, in addition to the radial orientation indication. (Marker 24 is more visible by x-ray than the nitinol needle)

Figure 13:
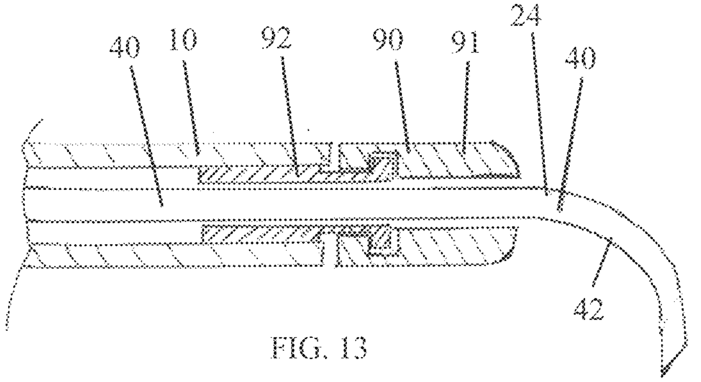
FIG. 13 is an illustration of the catheter tip having a swivel or articulating distal section.

Reference is now made to FIG. 13, which illustrates an alternative rigid tip 90 with a needle outlet 91, in which the needle 40 and catheter device 1 or catheter shaft 10 do not have any radial orientation mechanism. Instead needle 40 can rotate freely inside catheter shaft 10, preferably by turning or actuating an appropriate knob or other actuator on handle 30. Radiopaque marker 24 may be disposed on the needle distal section, e.g., near the distal end of straight section 41 proximal to the curved needle section 42. Marker 24 is used to indicate the axial location and angular orientation of curved needle section 42 only, since the rest of the needle is inside shaft 10. In this construction of device 1, there is no need for any needle protrusion orientation mechanism. An advantage of this embodiment over the other embodiments, is that in this embodiment needle 40 rotates completely inside shaft 10, which means there is no problem of potential friction between the catheter shaft 10 and blood vessels walls and/or stenotic blood vessel sections, which in the other embodiments, may prevent or disturb rotation of shaft 10. The only friction is between the catheter distal tip 90 and the curved needle section 42 due to section 42 being forced to be straight inside the distal tip. This friction can be drastically reduced by coupling the distal tip 90 to the distal end of shaft 10 with a bearing member 92, so that there is free rotation or articulation between distal tip 90 and shaft 10. The bearing member 92 may be fixed to the distal end of shaft 10. Due to bearing member 92, there is little or no resistance to rotation of needle 40 inside shaft 10.

Figure 14:
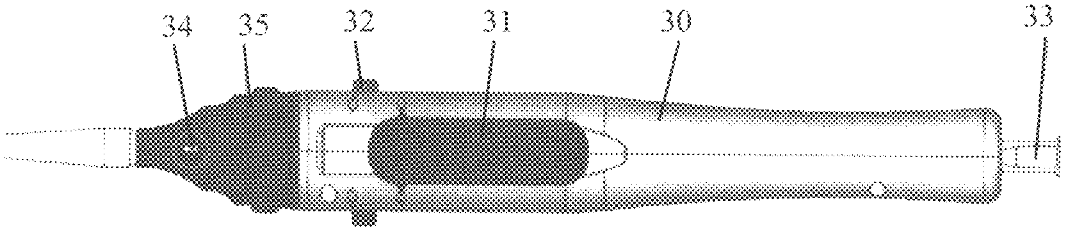
FIG. 14 is an illustration of the catheter handle with a needle protrusion length selector at a half-length position.

Reference is now made to FIG. 14. Handle 30 is connected to shaft 10. Handle 30 may include a needle axial slider 31 and a needle protrusion length selector 32. Slider 31 may be coupled to the proximal end of needle 40. Moving slider 31 forward (distally) causes protrusion of the sharp tip of needle 40 out from the catheter rigid tip. Moving slider 31 backwards pulls pre-curved needle 40 back inside the rigid tip.

Figure 15:
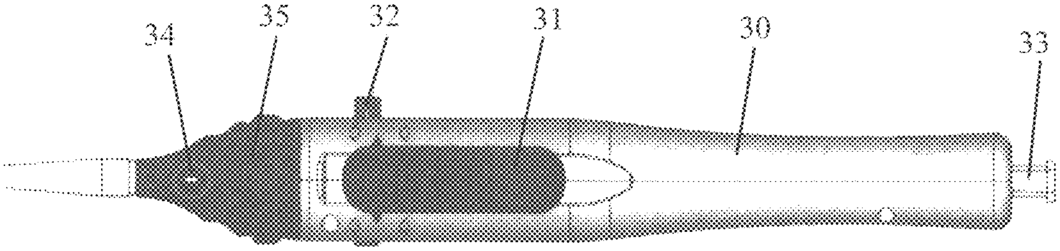
FIG. 15 is an illustration of the catheter handle with the needle protrusion length selector at the maximum needle length position.

Selector 32 is used as a needle protrusion limiter. In a first position of selector 32, the needle is locked and cannot protrude out of the catheter rigid tip. The selector may have several additional positions, including a second optional position to allow only small straight or almost straight needle section 43 to protrude out; a third position that allows half of the curved needle section to protrude out (as seen in FIG. 14); and fourth or final position to allow full curved needle distal section protrusion (as seen in FIG. 15). Selector 32 allows the user to quickly and easily select the length of curved needle section that protrudes from the device, using significant force that can be sufficient to cross hard plaque, while at the same time preventing moving the needle too far out which could damage nearby tissue or organs.

Handle 30 may include a luer port 33 for guidewire insertion, and optionally a luer 34 for flushing the catheter lumen. Luer 33 may be bonded to the proximal end of needle 40, and moves forward and backward together with needle 40.

Handle 30 may include a separate catheter or needle rotation knob 35 that rotates shaft 10 and/or needle 40, without rotating the whole handle 30.

When using the catheter device 1 of the invention as a crossing catheter, needle 40 only slightly protrudes forward, if straight or almost straight plaque puncture is required by needle lancet tip 44. If the puncture of the plaque is to be at an angle relative to the catheter axial direction, such as when the occlusion is bent or twisted, or if the catheter angular position is not correct, then needle 40 may be pushed further forward, until the needle protrudes at the correct angle, and the guidewire can be pushed forward in the correct direction.

When using the catheter device 1 of the invention as a reentry catheter, a guidewire is usually already placed in the sub-intimal space. The reentry catheter, with the needle positioned inside the rigid tip (20 or 50 or 60 or 90), is inserted over the guidewire until reaching the preferred reentry location. The guidewire is then pulled back a few centimeters.

The catheter (or the needle) is than rotated until the radiopaque marker is identified angiographically to be in the correct orientation, which is the needle bending direction, pointing towards the blood vessel true lumen. The needle is then pushed forward (e.g., using the slider in the handle), and the curved needle distal section penetrates the blood vessel walls, and enters the true lumen.

As mentioned above with reference to FIGS. 5A and 5B, if the true lumen is too distant, the whole catheter may be further pushed forward with the fully protruded needle, forcing the catheter distal section to follow the curved needle path and direction, until entering the true lumen. The guidewire is then pushed forward into the true lumen. After verifying that the guidewire is in the true lumen, the curved needle distal section is pulled back into the rigid distal tip, and the reentry catheter is pulled out from the patient.

What is claimed is:

1. A method comprising:

providing a catheter device comprising:

a straight catheter shaft comprising a lumen that extends straight through a distalmost end of said catheter shaft, wherein said catheter shaft lacks any side port;

a handle coupled to a proximal portion of said catheter shaft; and a needle that passes through said lumen in said catheter shaft and said distalmost end, said needle comprising a first straight section coupled to said handle, a curved section that extends distally from said first straight section, a second straight section that extends distally from said curved section, and a sharp distal tip at a most distal end of said needle, wherein said needle is made of an elastic material and, wherein when said needle is inside said lumen, said curved section becomes straight, and when said needle starts to protrude from said distalmost end, said sharp tip protrudes straight through said distalmost end and afterwards said second straight section protrudes straight through said distalmost end, and when said curved section exits said distalmost end, said curved section becomes curved again; and providing two steps for crossing an occlusion found in a true lumen of a blood vessel, a first step comprising:

advancing said needle without a guidewire in said catheter shaft so that only said sharp tip or said sharp tip and said second straight section protrude straight through said distalmost end; and using said sharp tip or said sharp tip and said second straight section of said needle to cross the occlusion without entering a sub-intimal space of the blood vessel; and a second step comprising:

further advancing said needle in said catheter shaft so that said curved section exits said distalmost end and said curved section becomes curved again;

using the curved section of said needle to cross the occlusion if the occlusion is at an angle relative to the catheter axial direction, with or without said curved section entering the sub-intimal space of the blood vessel; and wherein said needle is selectively advanced to penetrate the occlusion within the true lumen or to cross the occlusion within the sub-intimal space of the blood vessel and to reenter the true lumen.

2. The method according to claim 1, further comprising, when said curved section has exited said distalmost end and has become curved again, moving said curved section to advance said needle from the true lumen of the blood vessel into the sub-intimal space and then performing reentry into the true lumen from the sub-intimal space by advancing the catheter shaft distally with the needle fully or partially protruded from said catheter shaft, and moving said catheter, while said needle is fully or partially protruded, following a direction of the curved section, until said tip pierces and reenters the true lumen.

3. The method according to claim 2, wherein for reentry into the true lumen, said needle is fully protruded from said catheter shaft, and pulled back proximally if said needle has passed the true lumen, until the distal tip of said needle is positioned in the true lumen.

4. The method according to claim 2, wherein if the distal tip of said needle does not reach the true lumen for reentry into the true lumen, further comprising advancing said catheter shaft distally along said needle while fully or partially protruded, such that said catheter shaft follows a direction of said needle until said needle and said catheter shaft pierce and reenter the true lumen.

5. The method according to claim 1, wherein for crossing the occlusion, said needle is not fully protruded from said catheter shaft.

6. A catheter device comprising:

a straight catheter shaft comprising a lumen that extends straight through a distalmost end of said catheter shaft, wherein said catheter shaft lacks any side port;

a handle coupled to a proximal portion of said catheter shaft; and a needle that passes through said lumen in said catheter shaft and said distalmost end, said needle comprising a first straight section coupled to said handle, a curved section that extends distally from said first straight section, a second straight section that extends distally from said curved section, and a sharp tip at a most distal end of said needle, wherein said needle is made of an elastic material and, wherein when said needle without a guidewire is inside said lumen, said curved section becomes straight, and when said needle starts to protrude from said distalmost end, said sharp tip protrudes straight through said distalmost end and afterwards said second straight section protrudes straight through said distalmost end, and when said curved section exits said distalmost end, said curved section becomes curved again, and wherein, said needle is selectively advanceable to penetrate the occlusion within a true lumen of a blood vessel or to cross the occlusion within the sub-intimal space of the blood vessel and to reenter the true lumen.

7. The catheter device according to claim 6, wherein a distal portion of said catheter shaft and said needle form a keyed configuration for defining an angular orientation of said needle.

8. The catheter device according to claim 7, wherein said keyed configuration comprises a portion of said catheter shaft being formed with a longitudinal slot and said needle comprising a bulge arranged for sliding in said longitudinal slot, or said needle being formed with said longitudinal slot and a portion of said catheter shaft comprising said bulge.

* * * * *